(12) United States Patent
Yoshimoto et al.

(10) Patent No.: US 11,835,412 B2
(45) Date of Patent: Dec. 5, 2023

(54) DELICATE WORK TOOL DIGITALIZATION SYSTEM

(71) Applicant: Hitachi, Ltd., Tokyo (JP)

(72) Inventors: Hiroyuki Yoshimoto, Tokyo (JP); Ryotaro Kawahara, Tokyo (JP); Ryohei Matsui, Tokyo (JP); Nobuyuki Sugii, Tokyo (JP); Tsuneya Kurihara, Tokyo (JP); Hirohiko Sagawa, Tokyo (JP); Naoko Ushio, Tokyo (JP); Motoki Tajima, Tokyo (JP); Shingo Kirita, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 117 days.

(21) Appl. No.: 17/345,354

(22) Filed: Jun. 11, 2021

(65) Prior Publication Data

US 2021/0404895 A1  Dec. 30, 2021

(30) Foreign Application Priority Data

Jun. 26, 2020  (JP) .................................. 2020-110193

(51) Int. Cl.
*G01L 5/16* (2020.01)
*G01B 7/16* (2006.01)
*G01L 5/00* (2006.01)

(52) U.S. Cl.
CPC .................. *G01L 5/16* (2013.01); *G01B 7/18* (2013.01); *G01L 5/0095* (2013.01)

(58) Field of Classification Search
None
See application file for complete search history.

(56) References Cited

U.S. PATENT DOCUMENTS 5,467,656 A * 11/1995 Teare ...................... G01P 1/127
                                                         473/202
5,578,766 A * 11/1996 Kondo ...................... G01L 5/00
                                                         73/862.68

(Continued)

FOREIGN PATENT DOCUMENTS

CN        103097511 A        5/2013
CN        103565442 A        2/2014
(Continued)

OTHER PUBLICATIONS

Office Action issued in corresponding Chinese Patent Application No. 202110560613.0, with English Machine Translation dated Mar. 30, 2023 (19 pages).

*Primary Examiner* — Brandi N Hopkins
*Assistant Examiner* — Nigel H Plumb
(74) *Attorney, Agent, or Firm* — Foley & Lardner LLP

(57) ABSTRACT

Provided is a digitalization system capable of digitalizing the skills of delicate work. This digitalization system comprises a first sensor mounted on a work tool and which detects a deformation of the work tool when the work tool is pressed against a work target, a second sensor which detects a force applied to the work target or a force applied to the work tool when the work tool is pressed against the work target, and a computer which calculates an angle of a corner formed with the work tool and the work target based on sensor values acquired with the first sensor, and calculates a force applied to the work target when the work tool is pressed against the work target based on sensor values acquired with the second sensor.

9 Claims, 9 Drawing Sheets

(56) References Cited

U.S. PATENT DOCUMENTS

| | | | |
|---|---|---|---|
| 9,710,060 B2 * | 7/2017 | McMillen | G01L 1/18 |
| 10,362,989 B2 * | 7/2019 | McMillen | G01L 1/2293 |
| 10,646,153 B1 * | 5/2020 | Berme | A61B 5/1036 |
| 2001/0020937 A1 * | 9/2001 | Rosenberg | G01B 5/008 |
| | | | 345/184 |
| 2008/0127711 A1 * | 6/2008 | Farag | G01L 25/003 |
| | | | 73/1.11 |
| 2013/0109047 A1 | 5/2013 | Charrier et al. | |
| 2018/0049733 A1 * | 2/2018 | Zhao | G01L 5/102 |
| 2019/0134461 A1 * | 5/2019 | Segami | G01P 15/18 |

FOREIGN PATENT DOCUMENTS

| | | |
|---|---|---|
| CN | 206887130 U | 1/2018 |
| JP | H07-280672 A | 10/1995 |
| WO | WO-90/00293 A1 | 1/1990 |

* cited by examiner

DELICATE WORK TOOL DIGITALIZATION SYSTEM

TECHNICAL FIELD

The present invention generally relates to digitalization.

BACKGROUND ART

In the Japanese society, the number of young workers is decreasing. In light of this situation, measures such as the manpower saving of human work via mechanization, utilization of foreigners as manpower, utilization of elderly people, and utilization of diverse human resources are being taken. With this kind of background, in numerous fields of the manufacturing industry, demands of the digitalization of skills of human work for utilization in skill education and utilization in automated machine design are increasing.

For example, in the medical field, the understaffing of cell culture technicians to perform cell culture (culture operation work) based on manual operation is a bottleneck in performing such culture operation work, and demands of digitalizing the skills of culture operation work are increasing.

In response to the foregoing demands, considered may be a method of digitally extracting features from the video of culture operation work captured with a camera and the sensor values acquired from sensors for measuring the manual operation of the cell culture technician, and thereby identifying the bodily movement required for the cells to normally proliferate and providing feedback to the cell culture technician so as to urge the cell culture technician to conduct proper bodily movement.

Since culture operation work requires delicate bodily movement, a sensing system needs to be equipped with sensors in a manner which will not interfere with the culture operation work.

With respect to this point, a compact and inexpensive force detection/display device capable of being built into an operation tool or the like is disclosed (refer to PTL 1).

CITATION LIST

Patent Literature

[PTL 1] Japanese Unexamined Patent Application Publication No. H07-280672

SUMMARY OF THE INVENTION

Problems to be Solved by the Invention

With the force detection/display device described in PTL 1, it is possible to detect the force applied to the operation tool. Nevertheless, merely detecting the force applied to the operation tool is insufficient for digitalizing the skills of delicate work.

The present invention was devised in view of the foregoing points, and an object of this invention is to propose a digitalization system capable of digitalizing the skills of delicate work.

Means to Solve the Problems

In order to achieve the foregoing object, the present invention provides a digitalization system, comprising: a first sensor mounted on a work tool and which detects a deformation of the work tool when the work tool is pressed against a work target; a second sensor which detects a force applied to the work target or a force applied to the work tool when the work tool is pressed against the work target; and a computer which calculates an angle of a corner formed with the work tool and the work target based on sensor values acquired with the first sensor, and calculates a force applied to the work target when the work tool is pressed against the work target based on sensor values acquired with the second sensor.

With the foregoing configuration, the skills of delicate work can be digitalized, for example, by calculating the angle of the corner formed with the work tool and the work target and the force applied to the work target when the work tool is pressed against the work target.

Advantageous Effects of the Invention

According to the present invention, it is possible to digitalize the skills of delicate work.

DESCRIPTION OF EMBODIMENTS

(1) First Embodiment

Figure 1:
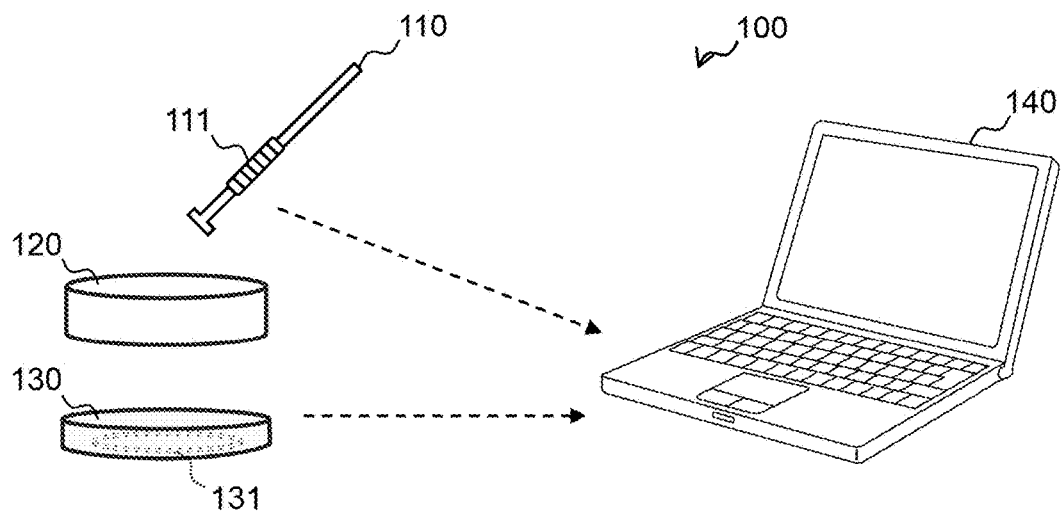
FIG. 1 is a diagram showing an example of the configuration of the digitalization system according to the first embodiment.

An embodiment of the present invention is now explained in detail. In this embodiment, the technology of digitalizing the skills of delicate work will be mainly explained. The present invention, however, is not limited to the following embodiment.

Delicate work is work that is performed using a work tool. As types of delicate work, considered may be adjustment work of products using instruments, assembly work of products using tools, culture work using a scraper, game play using a game machine controller, and golfing using golf clubs. In the following explanation, a case of performing culture work using a scraper will be taken as an example.

A scraper is used for scraping cultures from a container upon recovering cultures such as cells, tissues and bacterium cultured in a container such as a laboratory dish or a flask in the fields of cell culture, tissue culture, and bacterial culture. In the following explanation, a case of using a scraper for scaping cells from a laboratory dish upon recovering the cells cultured in a laboratory dish will be taken as an example.

An embodiment of the present invention is now explained with reference to the appended drawings. Note that, in the following explanation, the same number is assigned to the same elements in the drawings and the explanation thereof will be omitted as appropriate. Moreover, when the same types of elements are explained without being differentiated, the common part (part excluding the branch number) of the reference code including the branch number will be used, and when the same types of elements are explained by being differentiated, the reference code including the branch number may be used. For example, when the sensors are explained without any particular differentiation, they will be indicated as "pressure sensor 901", and when the individual sensors are explained by being differentiated, they may be indicated as "pressure sensor 901-1", "pressure sensor 901-2" and so on.

In FIG. 1, reference numeral 100 indicates the overall digitalization system according to the first embodiment.

FIG. 1 is a diagram showing an example of the configuration of the digitalization system 100.

The digitalization system 100 is a system of digitalizing the skills of work (recovery operation) where a worker recovers, in the culture process of cells, the cells attached to a laboratory dish 120 using a scraper 110 from the surface of the laboratory dish 120.

More specifically, the digitalization system 100 comprises a scraper 110 for recovering cells, a stand 130 on which is mounted the laboratory dish 120 in which cells are cultured, and a computer 140 which performs various types of processing.

The scraper 110 is a work tool for recovering, from the laboratory dish 120, cells attached to the surface of the laboratory dish 120. A bend sensor 111 is mounted on the scraper 110. The bend sensor 111 is a resistor in which the electrical resistance value increases when bent, and detects the bending of the scraper 110 when the worker presses the scraper 110 against the laboratory dish 120. The sensor values acquired with the bend sensor 111 are sent to the computer 140 via wired or wireless communication.

The laboratory dish 120 (body) is a flat dish made of glass used for cell culture in inspections and experiments. As the laboratory dish 120, a commercially available laboratory dish may be used. The shape (round, oval, square, etc.), size, and material (glass, plastic, stainless steel, Teflon (registered trademark), alumite, etc.) of the laboratory dish 120 may be arbitrarily adopted. The illustration and explanation of the lid of the laboratory dish 120 have been omitted.

The stand 130 is a stand for mounting the laboratory dish 120 thereon. The stand 130 comprises a pressure sensor 131. The pressure sensor 131 detects a force when the laboratory dish 120 is mounted on the stand 130 by a worker and the scraper 110 is pressed against the laboratory dish 120; to put it differently, a force of the stand pressing the contact surface (for example, work table) of the stand 130 as a result of the laboratory dish 120 pressing the stand 130 when the scraper 110 is pressed against the laboratory dish 120. The sensor values acquired with the pressure sensor 131 are sent to the computer 140 via wired or wireless communication.

The computer 140 is a laptop computer, a tablet terminal, a server device or the like. The computer 140 calculates (extracts) and stores the inclination (pressing angle) of the scraper 110 during work from the sensor data (bend data) indicating the sensor values acquired with the bend sensor 111. Moreover, the computer 140 calculates (extracts) and stores the force (pressing strength) of the scraper 110 pressing against the laboratory dish 120 from the sensor data (pressure data) indicating the sensor values acquired with the pressure sensor 131.

Note that, while not shown, the computer 140 comprises a processor, a main storage device, an auxiliary storage device, an input device, an output device, and a communication device.

The processor is a device for performing arithmetic processing. The processor is, for example, a CPU (Central Processing Unit), an MPU (Micro Processing Unit), a GPU (Graphics Processing Unit), an AI (Artificial Intelligence) chip or the like.

The main storage device is a device for storing programs, data and the like. The main storage device is, for example, a ROM (Read Only Memory), a RAM (Random Access Memory) or the like. The ROM is an SRAM (Static Random Access Memory), an NVRAM (Non Volatile RAM), a Mask ROM (Mask Read Only Memory), a PROM (Programmable ROM) or the like. The RAM is a DRAM (Dynamic Random Access Memory) or the like.

The auxiliary storage device is an HDD (Hard Disk Drive), a flash memory, an SSD (Solid State Drive), an optical storage device or the like. The optical storage device is a CD (Compact Disc), a DVD (Digital Versatile Disc) or the like. The programs and data stored in the auxiliary storage device are read into the main storage device as needed.

The input device is a user interface for receiving information from the user. The input device is, for example, a keyboard, a mouse, a card reader, a touch panel or the like.

The output device is a user interface for outputting (display output, audio output, print output, etc.) various types of information. The output device is, for example, a display device, an audio output device (speaker), a printing device or the like which visualizes various types of information. The display device is an LCD (Liquid Crystal Display), a graphic card or the like.

The communication device is a communication interface for communicating with other devices via a communication medium. The communication device is, for example, an NIC (Network Interface Card), a wireless communication module, a USB (Universal Serial Interface) module, a serial communication module or the like. The communication device can also function as an input device for receiving information from other devices which are communicably connected. Moreover, the communication device can also function as an output device for sending information to other devices which are communicably connected.

The various functions (bend communication unit 221, pressure communication unit 222, processing unit 223, determination unit 224, result storage unit 225, history storage unit 226 and the like described later) equipped in the computer 140 are realized by the processor reading and executing the programs stored in the main storage device, or with the hardware (FPGA, ASIC, AI chip, etc.) configuring the computer 140.

Figure 2:
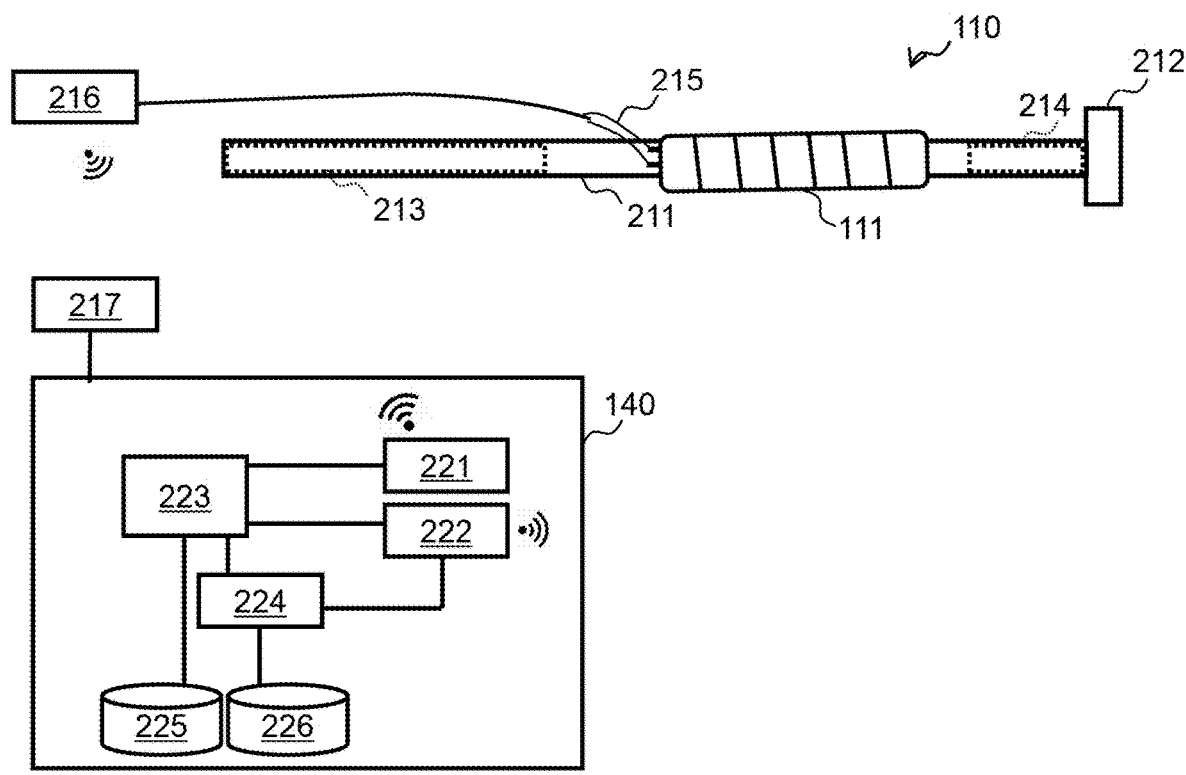
FIG. 2 is a diagram showing an example of the configuration of the scraper according to the first embodiment.

FIG. 2 is a diagram showing an example of the configuration of the scraper 110.

As shown in FIG. 2, the scraper 110 is of a T-shaped structure. More specifically, the scraper 110 is configured from a handle 211 and a blade 212.

The handle 211 is an elastic body which deforms when external force is applied thereto. When the worker presses the scraper 110 against the laboratory dish 120, the handle 211 flexibly bends without breaking. For example, the handle 211 is a plastic molded object. The material of the handle 211 may be ABS resin, rigid PVC, polypropylene, polyethylene, polystyrene, polyester, TPX resin or the like, and there is no particular limitation so long as it has a certain level of strength.

The overall shape of the handle 211 is a rod shape, and the handle 211 is provided with a gripping part 213 to be gripped by the worker, and a blade 212 is provided to a tip part 214 on the opposite end.

The blade 212 is the region that closely adheres to the culture surface of the laboratory dish 120. The blade 212 is formed from a rubber-like elastic body material. The material of the blade 212 may be silicone rubber, fluoro rubber or the like, and there is no particular limitation so as long as it does not have cell toxicity.

The method of using the scraper 110 is now explained. Since the scraper 110 is housed in a sterilization bag, the worker foremost removes the scraper 110 from the sterilization bag. The worker thereafter causes the blade 212 to closely adhere to the culture surface of the laboratory dish 120, and scrape the cells by repeatedly pulling the handle 211 toward oneself. The blade 212 is formed from a rubber-like elastic body material and is soft, and will not damage the cell tissues. When the worker completes scraping the cells, the worker adds a culture medium in the laboratory dish 120, exposes the scraped cells in the laboratory dish 120 via washing outside the laboratory dish 120, and then ends the sequential recovery operation.

Moreover, the scraper 110 is provided with a bend sensor 111 from near the center of the handle 211 to the tip part 214 toward the blade 212. A signal line 215 for transmitting electric signals is connected to the bend sensor 111. A control device 216 is connected to the signal line 215. The control device 216 comprises a communication device, an ADC (Analog to Digital Converter), a power supply unit and the like. The control device 216 digitizes the analog bend signals (sensor values) and sends the digitized sensor values to the computer 140.

An NTP (Network Time Protocol) server device 217 is connected to the computer 140 via a communication network. The computer 140 is receiving current time information from the NTP server device 217.

The computer 140 comprises a bend communication unit 221, a pressure communication unit 222, a processing unit 223, a determination unit 224, a result storage unit 225, and a history storage unit 226.

The bend communication unit 221 performs wireless communication with the control device 216. The bend communication unit 221 receives bend data sent from the bend sensor 111 (control device 216). The pressure communication unit 222 performs wireless communication with the stand 130. The pressure communication unit 222 receives pressure data sent from the stand 130. Note that the method (radio waves) of wireless communication may be a digital method (digital radio waves) or an analog method (analog radio waves).

The processing unit 223 calculates a pressing angle from the bend data notified from the bend communication unit 221. The result storage unit 225 links the data of the pressing angle calculated by the processing unit 223 with the current time, and stores the linked pressing angle data and current time. Note that the calculation method of the pressing angle will be explained later with reference to FIG. 7. Moreover, the result storage unit 225 links the pressure data sent from the stand 130, as the data of the pressing strength, with the current time, and stores the linked pressure data and current time.

The determination unit 224 checks the work description of the worker from the data (pressing angle data and pressing strength data) calculated by the processing unit 223. For example, the determination unit 224 checks the work description by comparing the data indicating the standard work stored in the history storage unit 226 and the calculated data. In other words, the determination unit 224 determines whether the work is correct/incorrect by determining whether the work performed by the worker was standard work or work that deviated from the standard work. Note that "standard work" may be the work performed according to a manual or the work performed by a skilled worker.

For example, when the scraper 110 is bent considerably despite weak force being applied to the laboratory dish 120 (stand 130), the determination unit 224 estimates that the scraper 110 is being pressed against the laboratory dish 120 at an angle that is close to horizontal. Meanwhile, when the scraper 110 is not bent that much despite strong force being applied to the laboratory dish 120 (stand 130), the determination unit 224 estimates that the scraper 110 is being pressed against the laboratory dish 120 at an angle that is close to vertical.

Subsequently, upon comparing the estimated description (work) with the standard work, for example, the determination unit 224 sends a first determination result, which indicates that the pressing angle is too horizontal, to the stand 130 upon determining that the pressing angle is too horizontal, and sends a second determination result, which indicates that the pressing angle is too vertical, to the stand 130 upon determining that the pressing angle is too vertical.

The determination result includes information indicating whether the work is correct/incorrect. Information indicating whether the work is correct/incorrect is notification information such as a lighting pattern of an LED, color of an LED, vibration pattern of a vibrator, or intensity of vibration of a vibrator. Note that, with the digitalization system 100, notification information is prepared in advance in correspondence with the determination result. When the stand 130 receives a determination result, the stand 130 notifies the worker in the mode according to the determination result.

Note that the determination performed by the determination unit 224 is not limited to the determination described above. The determination unit 224 may compare the pressing angle of the scraper 110 and the pressing angle in the standard work, or compare the pressing strength of the scraper 110 and the pressing strength in the standard work, or compare the pressing time of the scraper 110 and the pressing time in the standard work, or compare the pressing rhythm of the scraper 110 (combination of time that pressing is strong and time that pressing is weak) and the pressing rhythm in the standard work, or perform the comparison based on the combination of the above.

Note that one function of the computer 140 may be divided into a plurality of functions, or a plurality of functions may be consolidated into one function. Moreover, a part of the functions of the computer 140 may be provided as a separate function, or included in another function. Moreover, a part of the functions of the computer 140 may be realized with another computer which is communicably connected to the computer 140.

Figure 3:
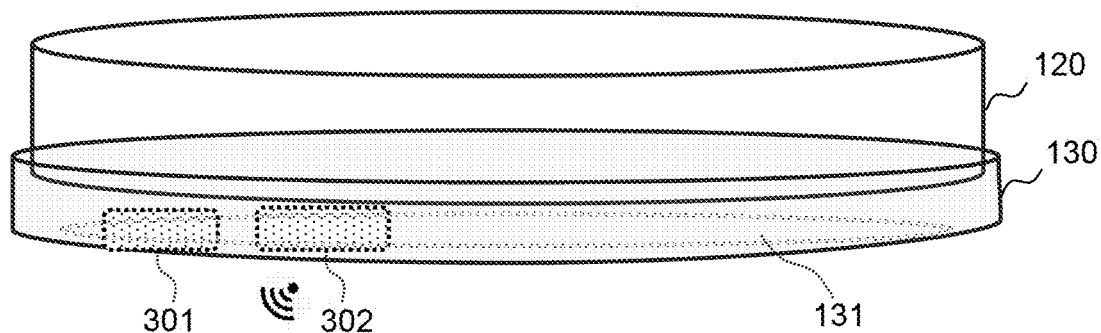
FIG. 3 is a diagram showing the main configuration of the stand according to the first embodiment.

The stand 130 is now explained with reference to FIG. 3 to FIG. 5. FIG. 3 is a diagram showing the main configuration of the stand 130.

The stand 130 is a stand for mounting the laboratory dish 120 thereon. The stand 130 comprises a pressure sensor 131, a battery 301, and a communication device 302. The pressure sensor 131, the battery 301 and the communication device 302 are connected via a signal line (not shown).

The pressure sensor 131 is provided to a bottom part 501 of the stand 130; more specifically, provided to a contact surface of the stand 130 in contact with a work table (not shown) on which the stand 130 is mounted. The pressure sensor 131 measures a force of the stand 130 pressing against the work table. The sensor values measured by the pressure sensor 131 are sent in real-time from the communication device 302 to the computer 140.

Details of the stand 130 are now explained with reference to FIG. 4 and FIG. 5. FIG. 4 is an image diagram when the stand 130 is viewed from directly above. FIG. 5 is an image diagram when the stand 130 is viewed directly from the side.

Figure 4:
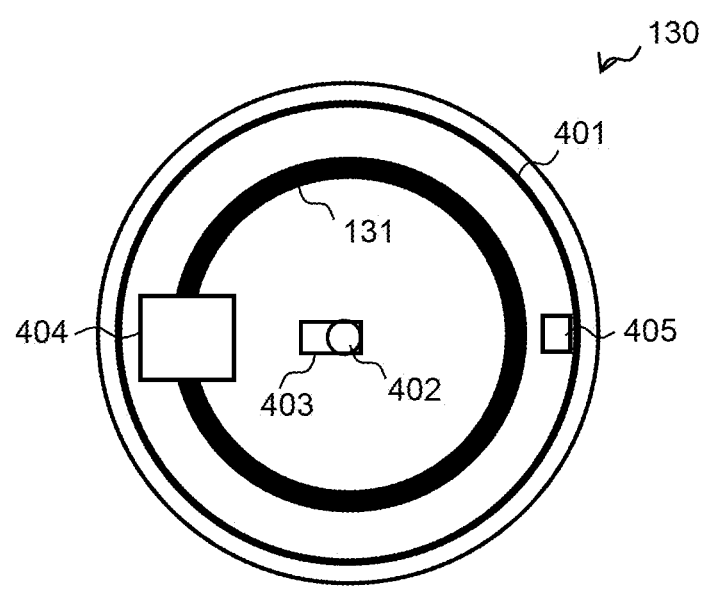
FIG. 4 is a diagram when the stand according to the first embodiment is viewed from directly above.

As shown in FIG. 4, the stand 130 comprises a rubber ring 401, a suction port 402, a backflow prevention valve 403, a printed circuit board 404, and a notification unit 405.

Figure 5:
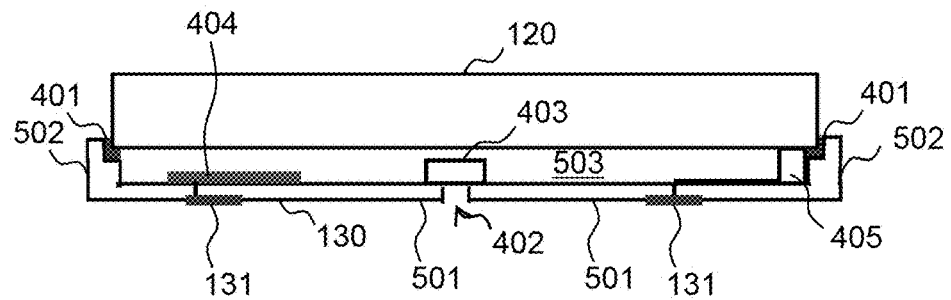
FIG. 5 is a diagram when the stand according to the first embodiment is viewed directly from the side.

As shown in FIG. 5, the overall shape of the stand 130 is a concave shape. More specifically, the stand 130 comprises a bottom part 501, and a peripheral wall part 502 formed at the outer edge part of the bottom part 501. The laboratory dish 120 is mounted on the concave part of the peripheral wall part 502.

The rubber ring 401 is a ring-type mechanical component having an L-shaped cross section. The rubber ring 401 is a component provided in the concave part for sealing the air in a space 503 formed as a result of the laboratory dish 120 being mounted on the stand 130. To put it differently, the space 503 is a sealed space formed with the stand 130 and the laboratory dish 120.

The suction port 402 is a through-hole that is used when sucking the air inside the space 503. A backflow prevention valve 403 is provided to the suction port 402. The backflow prevention valve 403 comprises a function of allowing a fluid (for example, air) to flow from the suction port 402 toward the outside of the space 503, and preventing the fluid from flowing from the suction port 402 toward the inside of the space 503.

The printed circuit board 404 is configured by including a battery 301, a communication device 302, an inertial sensor, a temperature sensor, a humidity sensor and the like. The inertial sensor is a sensor which performs measurement using inertia, and measures the worker's recovery operation performed to the laboratory dish 120. The inertial sensor is an acceleration sensor, a gyro sensor, a geomagnetic sensor or the like. According to the inertial sensor, the type of action taken against the laboratory dish 120 (culture) can be detected, and the skills of the recovery operation can be digitalized with greater accuracy.

The notification unit 405 performs notification based on the determination result sent from the computer 140. The notification unit 405 comprises, for example, an LED (Light Emitting Diode). The notification unit 405 lights the LED according to the determination result. Note that the lighting pattern of the LED and the lighting color of the LED are prescribed in advance in correspondence with the result of whether the recovery operation is correct/incorrect.

For example, when a determination result is notified, the notification unit 405 lights the bottom face of the laboratory dish 120 and makes the culture, which is being observed by the worker, difficult to see, and thereby causes the worker to notice whether the recovery operation is correct/incorrect. Here, for example, when the first determination result is notified, the notification unit 405 lights the bottom face of the laboratory dish 120 in red and notifies the worker that the pressing angle is too horizontal. Moreover, for example, when the second determination result is notified, the notification unit 405 lights the bottom face of the laboratory dish 120 in yellow and notifies the worker that the pressing angle is too vertical.

With the digitalization system 100, the bottom face of the laboratory dish 120 is configured from frosted glass and, as a result of lighting a part thereof, the overall bottom face of the laboratory dish 120 is lit. Note that the configuration may also be such that the notification unit 405 is provided to be positioned at the center of the laboratory dish 120, and the center of the laboratory dish 120 is lit. Moreover, when a determination result is notified, the notification unit 405 may also be configured such that the result of whether the recovery operation is correct/incorrect is notified to the worker, for example, by lighting the peripheral wall part 502 of the laboratory dish 120. According to the foregoing configuration, it is possible to notify the worker of whether the recovery operation is correct/incorrect without affecting the culture with light.

Since the feedback of erroneous work, such as an error in the pressing angle or the pressing strength of the scraper 110, is provided by the notification unit 405 to the worker, the worker can correct such error on site, and will be able to perform the recovery operation more properly.

Figure 6:
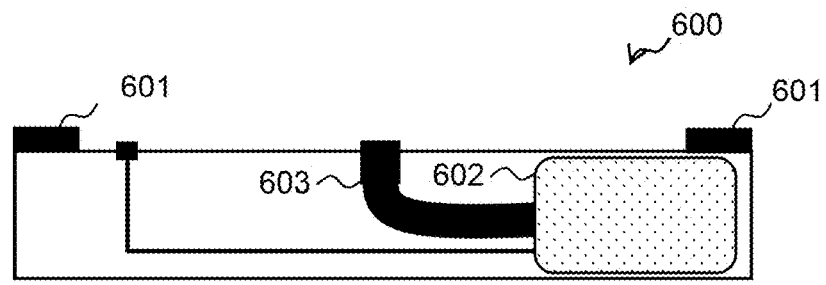
FIG. 6 is a diagram showing an example of the suction device according to the first embodiment.

FIG. 6 is a diagram showing an example of the suction device 600.

The suction device 600 is a device for causing the space 503 to be a vacuum; that is, a state filled with gas of a pressure that is lower than normal atmospheric pressure. The suction device 600 is configured to match the size of the stand 130, and the stand 130 can be mounted on the suction device 600. The suction device 600 comprises a rubber ring 601, a small pump 602, and a tube 603.

The rubber ring 601 is a ring-type mechanical component having a rectangular cross section, and is a component on which the stand 130 is mounted. The small pump 602 is a vacuum pump. The tube 603 is connected to the small pump 602, and the tube 603 is also connected to a suction port 402. The small pump 602 sucks air from the space 503 through the tube 603.

The relation of the laboratory dish 120, the stand 130 and the suction device 600 is now explained. If the laboratory dish 120 is merely fitted into the concave part of the stand 130, the laboratory dish 120 will easily become dislodged. Thus, the worker uses the suction device 600 to suck the air of the space 503 and create a vacuum. In other words, the stand 130 vacuum-sucks the laboratory dish 120. After the vacuum suction is complete, the worker removes the suction device 600 from the stand 130, mounts the stand 130 on the work table, and thereby performs the recovery operation. During the recovery operation, the laboratory dish 120 and the stand 130 are integrated without being separated. After the recovery operation is complete, the worker raises the end of the rubber ring 401 and lets air into the space 503 upon removing the laboratory dish 120 from the stand 130. Note that the method of removing the laboratory dish 120 from the stand 130 may also be a method of pumping air with a pump or the like.

Figure 7:
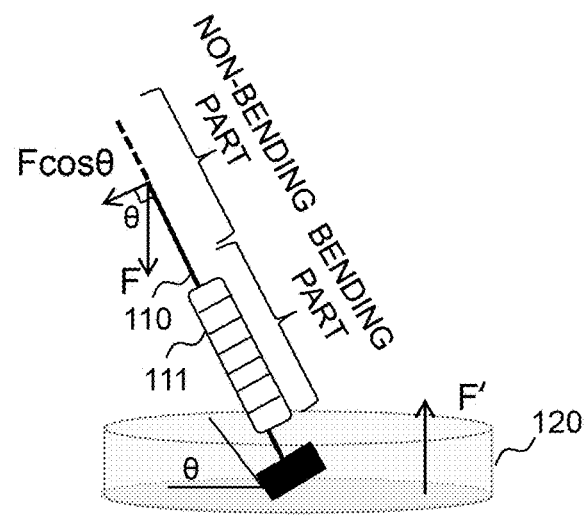
FIG. 7 is a diagram showing an example of the mode of using the scraper according to the first embodiment.
Figure 8:
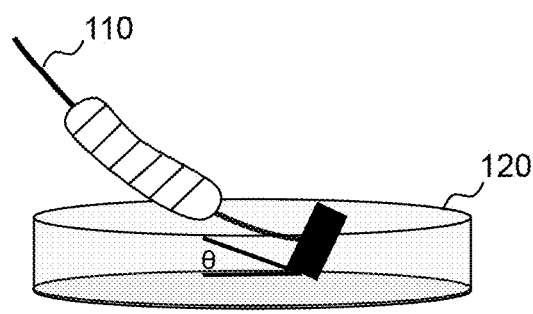
FIG. 8 is a diagram showing an example of the mode of using the scraper according to the first embodiment.

The mode of using the scraper 110 is now explained with reference to FIG. 7 and FIG. 8. FIG. 7 and FIG. 8 are diagrams showing an example of the mode of using the scraper 110.

As shown in FIG. 7, the weaker the pressing strength to the laboratory dish 120, or the closer the pressing angle is to 90 degrees, the bending of the scraper 110 will be smaller. Moreover, as shown in FIG. 8, the stronger the pressing strength to the laboratory dish 120, or the closer the pressing angle is to 0 degrees, the bending of the scraper 110 will be greater. To put it differently, when the pressing strength to the laboratory dish 120 is the same strength, the scraper 110 will bend more when the pressing angle is smaller, and, when the pressing angle is the same angle, the scraper 110 will bend more when the pressing strength to the laboratory dish 120 is greater.

The calculation method of the pressing angle of the scraper 110 is now explained.

In FIG. 7, 8 indicates the angle (pressing angle) of the corner formed with the scraper 110 and the laboratory dish 120. F indicates the force (pressing strength) applied by the scraper 110 in the vertical direction of the laboratory dish 120. F' indicates the counteracting force (resistance) of the laboratory dish 120 applied to the scraper 110. Note that, based on the law of action and reaction, F=F'.

Here, when the bending amount M of the scraper 110 is expressed with a function $f(X)$ of a force X applied in a direction that is orthogonal to the horizontal surface of the scraper 110 at a non-bending part, the bending amount M=f(F cos θ). Based on the foregoing formula, the formula for calculating the corner 8 formed with the scraper 110 and the laboratory dish 120 will be as follows.

$$\theta = \cos^{-1}(f^{-1}(M)/F)$$

Note that F is calculated based on the counteracting force F' applied to the laboratory dish 120 of the scraper 110 or to the worker's body. Moreover, M can be calculated based on the sensor values acquired with the bend sensor 111. Thus, 8 can be calculated based on the foregoing formula. Note that, generally speaking, since bending will be greater as the applied force is greater, f(X) will be a monotonically increasing function of X.

According to this embodiment, the skills of culture work can be digitalized. More specifically, the skills of a worker's recovery operation, which is difficult to extract with a camera, can be digitalized. For example, the skills of a worker's recovery operation can be digitalized by measuring the pressing angle of the worker's hand, which cannot be captured with a camera, and the pressing strength, which is difficult to estimate from the video captured with a camera. Moreover, for example, by providing feedback to the worker in real-time based on the digitized data, efficiency of the recovery operation can be improved. Moreover, for example, by accumulating the digitized data, the worker can look back on the recovery operation, and this can be utilized in the education of workers.

(2) Second Embodiment

This embodiment differs from the first embodiment with regard to the configuration of measuring the pressing strength of the scraper 110. In this embodiment, the same configuration as the first embodiment is given the same symbol, and the explanation thereof is omitted as appropriate.

In this embodiment, the pressing strength of the scraper 110 is measured with a glove with built-in sensors 900 worn by the worker in substitute for the pressure sensor 131. As a result of the worker performing the recovery operation, the glove with built-in sensors 900 senses the pressing strength of the scraper 110.

The sensor values acquired with the glove with built-in sensors 900 are sent to the computer 140, whether the recovery operation is correct/incorrect is determined, and the determination result is returned to the glove with built-in sensors 900. Since the glove with built-in sensors 900 outputs the determination result and provides feedback of erroneous work, such as an error in the pressing angle or the pressing strength of the scraper 110, to the worker, the worker can correct such error on site, and will be able to perform the recovery operation more properly.

Figure 9:
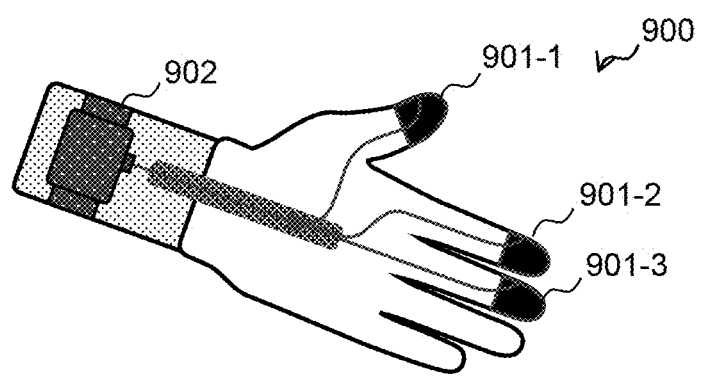
FIG. 9 is a diagram showing an example of the glove with built-in sensors according to the second embodiment.

FIG. 9 is a diagram showing an example of the glove with built-in sensors 900.

The glove with built-in sensors 900 comprises a pressure sensor 901-1 mounted at the position of the thumb, a pressure sensor 901-2 mounted at the position of the index finger, a pressure sensor 901-3 mounted at the position of the middle finger, and an information processing device 902 mounted at the position of the wrist. The pressure sensor 901 senses the force of grabbing something or pressing something with fingers. The information processing device 902 has a microphone, a communication device, a vibrator and the like built therein, and the information processing device 902 sends sensor values (pressure data) to the computer 140.

When the worker wears the glove with built-in sensors 900 and grips the scraper 110, pressure data of the thumb, pressure data of the index finger, and pressure data of the middle finger will all increase. Moreover, a characteristic sound of the recovery operation is simultaneously detected with a microphone. When the recovery operation is complete, pressure data of the thumb, pressure data of the index finger, and pressure data of the middle finger will all decrease, and the characteristic sound acquired with the microphone will simultaneously stop.

Here, the determination unit 224 of the computer 140 identifies the start of the recovery operation, for example, when three types of pressure data simultaneously increase at a certain time and a characteristic sound is detected with a microphone, and identifies the completion of the recovery operation upon detecting that the high pressure data and the characteristic sound have both stopped after the lapse of a given period of time. Note that, with the microphone sound, the characteristic sound may be detected, for example, by using an intensity in a specific frequency of the sound.

Moreover, the determination unit 224 determines whether the recovery operation is correct/incorrect by comparing the pressing angle of the scraper 110, the pressing strength of the scraper 110 (strength of gripping the scraper 110 with fingers), the pressing time of the scraper 110, the pressing rhythm of the scraper 110, and abnormal sounds mixed in the sound during the recovery operation with the data indicating the standard work.

The information processing device 902 comprises a vibrator as a notification unit for notifying the result of the determination by the computer 140. The information processing device 902 generates a vibration with the vibrator according to the result of the determination.

Note that the glove with built-in sensors 900 may be of a cap shape to be placed on the fingertips, or of a shape of covering the palm or back of the hand.

In the assembly process of manufacturing, there are cases where it is not possible to mount a pressure sensor on the work target to which the work tool is pressed in factories or the like where products are being assembled. Even in the foregoing case, since pressure sensors can be mounted on the worker's body according to this embodiment, the pressing strength of the work tool can be measured.

(3) Third Embodiment

This embodiment differs from the first embodiment with regard to the configuration of the bend sensor being detachably fixed to the scraper. In this embodiment, the same configuration as the first embodiment is given the same symbol, and the explanation thereof is omitted as appropriate.

Figure 10:
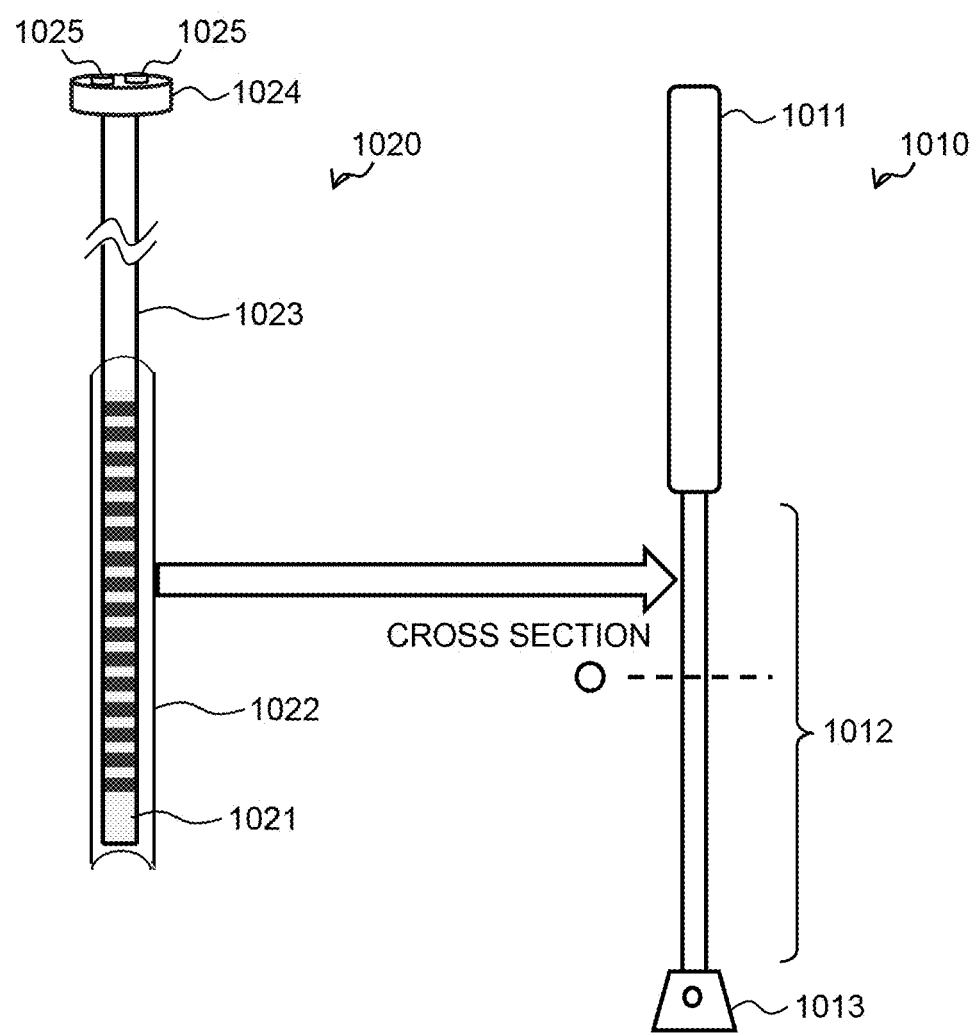
FIG. 10 is a diagram showing an example of the configuration of the sensor unit according to the third embodiment.
Figure 11:
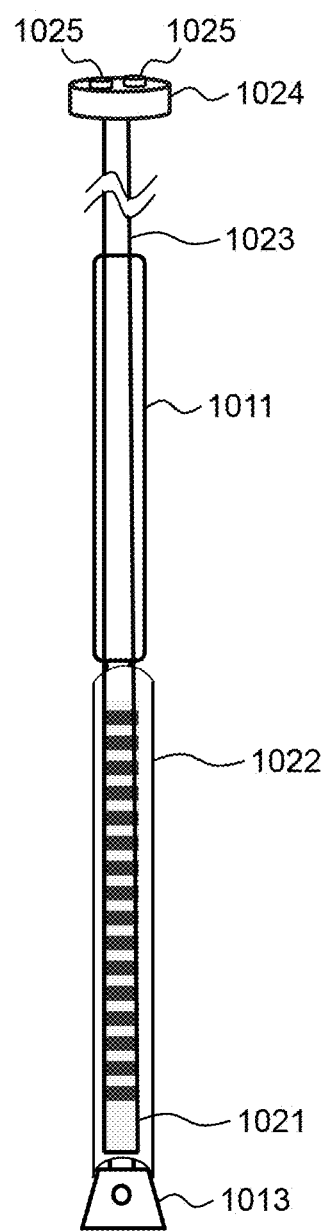
FIG. 11 is a diagram showing an example of the mode of using the scraper according to the third embodiment.
Figure 12:
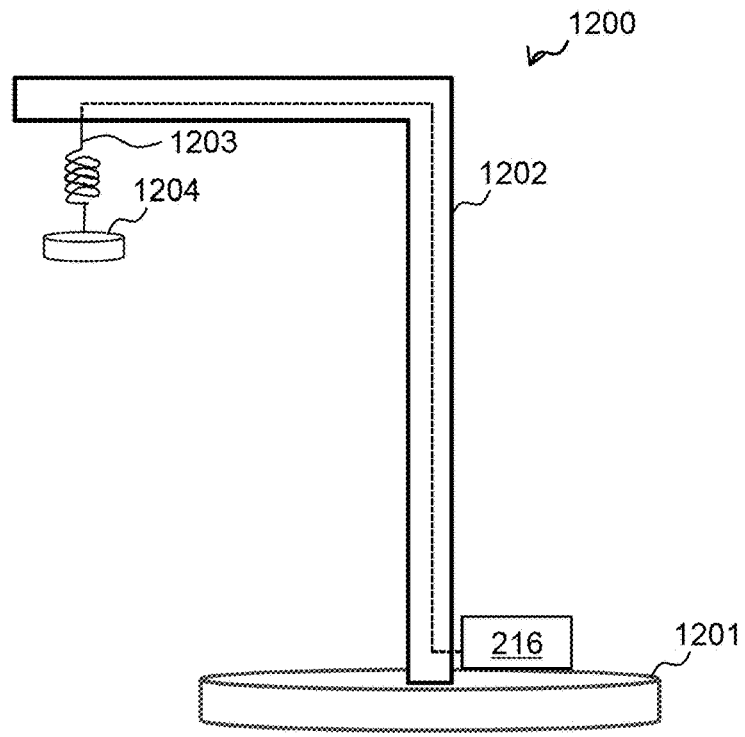
FIG. 12 is a diagram showing an example of the suspension stand according to the third embodiment.

As shown in FIG. 10 to FIG. 12, the digitalization system 100 comprises a scraper 1010, a sensor unit 1020 that can be attached to and detached from the scraper 1010, and a suspension stand 1200 for suspending the sensor unit 1020.

FIG. 10 is a diagram showing an example of the configuration of the sensor unit 1020.

The scraper 1010 comprises a gripping part 1011 as the part to be gripped by the worker, a mounting part 1012 on which the sensor unit 1020 is mounted, and a blade 1013 which adheres to the laboratory dish 120 and scrapes the cells on the laboratory dish 120. Note that the scraper 1010 is not limited to the foregoing configuration, and an arbitrary scraper that is commercially available may also be used.

The sensor unit 1020 comprises a bend sensor 1021, a film 1022, a signal line 1023, and a magnet 1024.

A film 1022 (glue film, self-adhesive film, etc.), which is rounded and slightly larger than the bend sensor 1021, is provided to the bend sensor 1021. The inside of the film 1022 has adhesive strength, and the film 1022 is affixed to the mounting part 1012 having a round cross section.

FIG. 11 is a diagram showing an example of the mode of using the scraper 1010 when the sensor unit 1020 is mounted on the scraper 1010.

Since the film 1022 of the sensor unit 1020 does not cover the gripping part 1011 when it is mounted on the mounting part 1012, the bend sensor 1021 and the film 1022 will not get in the way when the worker grips the scraper 1010.

Moreover, since the worker can remove the sensor unit 1020 from the scraper 1010, the scraper 1010 and the sensor unit 1020 can be replaced easily, and the cleanliness of the recovery operation can be maintained.

FIG. 12 is a diagram showing an example of the suspension stand 1200.

The suspension stand 1200 comprises a base part 1201, a pillar member 1202 erected on the base part 1201, a signal line 1203, and a magnet 1204.

The pillar member 1202 is erected from the center of the base part 1201, and the end of the pillar member 1202 forms an arm part which is bent and extends in a horizontal direction. The control device 216 is connected to one end of the signal line 1203, the signal line 1203 is suspended downward from the lower surface side near the tip of the arm part via the pillar member 1202, and the magnet 1204 is mounted on the other end of the signal line 1203.

The material of the base part 1201 and the pillar member 1202 may be ceramic, metal, plastic, wood or the like, and there is no particular limitation so as long as it has a certain level of strength and weight.

Figure 13:
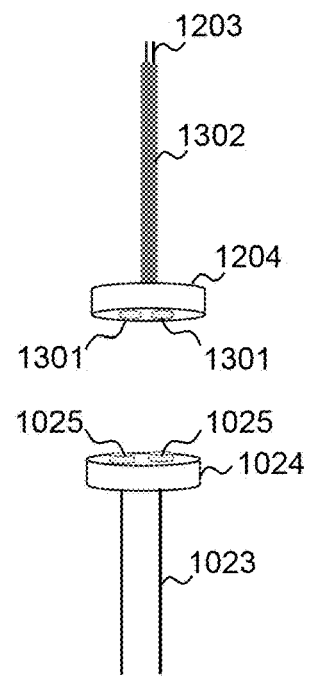
FIG. 13 is a diagram showing an example of the magnets according to the third embodiment.

FIG. 13 is a diagram showing an example of the magnets 1024, 1204.

The magnet 1024 includes a convex part 1025. The magnet 1204 includes a concave part 1301. The magnet 1024 and the magnet 1204 are structured to stick together as a result of the convex part 1025 being fitted into the concave part 1301.

According to the foregoing structure, it is possible to avoid a situation where the magnet 1024 and the magnet 1204 are shifted to the side in the recovery operation. Moreover, according to the foregoing structure, since the worker can remove the sensor unit 1020 from the suspension stand 1200 by pulling the scraper 1010 vertically, the scraper 1010 and the sensor unit 1020 can be replaced easily, and the cleanliness of the recovery operation can be maintained.

Furthermore, the signal line 1203 may also be housed in a cable 1302.

Note that the magnet 1024 may also be a ferromagnetic material such as iron that will be drawn toward the magnet 1204. Moreover, the magnet 1024 does not need to comprise the convex part 1025. In the foregoing case, the sensor unit 1020 may be suspended from an iron beam or an iron ceiling rather than from the suspension stand 1200.

Figure 14:
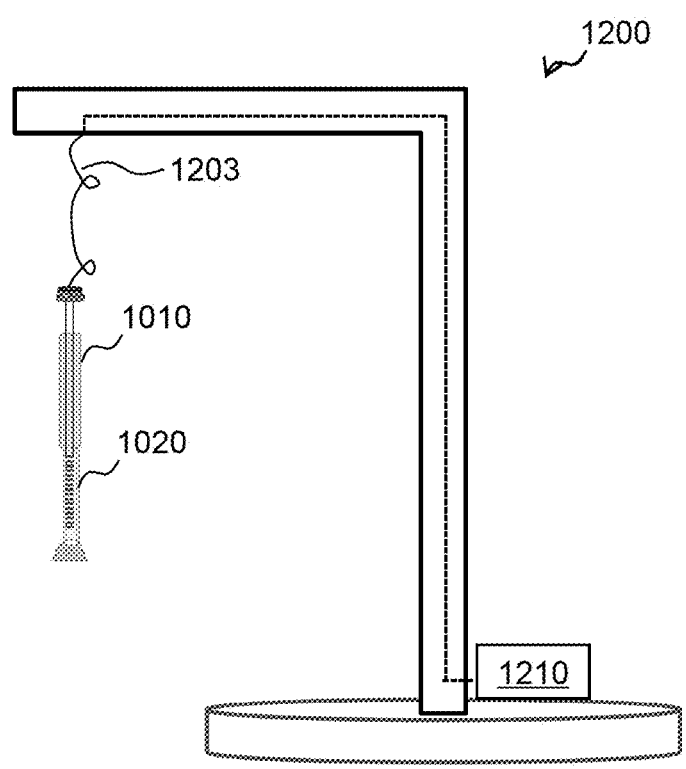
FIG. 14 is a diagram showing an example of the mode of using the suspension stand according to the third embodiment.

FIG. 14 is a diagram showing an example of the mode of using the suspension stand 1200.

The suspension stand 1200 is used by being mounted on a work table (not shown) or the like. Here, as a result of the magnet 1024 being mounted on the magnet 1204, the scraper 1010 to which the sensor unit 1020 has been affixed will be suspended. While the worker will perform the recovery operation in a state where the scraper 1010 is connected to the suspension stand 1200, since the signal line 1203 possesses elastic properties, the workability of the recovery operation will not be impaired. Moreover, after the recovery operation is complete, the scraper 1010 and the sensor unit 1020 will be stably maintained in a suspended state due to gravity.

In this embodiment, the sensor unit 1020 can be attached to and detached from the scraper 1010. Thus, since the worker can remove the sensor unit 1020 from the scraper 1010, the scraper 1010 and the sensor unit 1020 can be replaced easily, and the cleanliness of the recovery operation can be maintained.

(4) Fourth Embodiment

This embodiment differs from the third embodiment with regard to the configuration of the bend sensor being mounted on the scraper. In this embodiment, the same configuration as the first embodiment and the third embodiment is given the same symbol, and the explanation thereof is omitted as appropriate.

Figure 15:
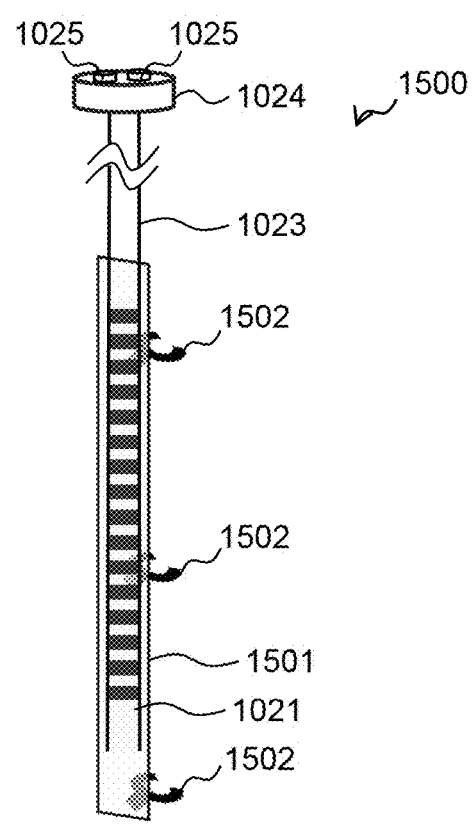
FIG. 15 is a diagram showing an example of the configuration of the sensor unit according to the fourth embodiment.

FIG. 15 is a diagram showing an example of the configuration of the sensor unit 1500.

The sensor unit 1500 comprises a bend sensor 1021, a signal line 1023, a magnet 1024, a film 1501, and one or more hooks 1502 for mounting the bend sensor 1021 on the scraper 1010.

A film 1501, which is rounded and slightly larger than the bend sensor 1021, is provided to the bend sensor 1021. Hooks 1502 are provided to the inside of the film 1022, and the film 1022 is mounted on the mounting part 1012. Note that there is no particular limitation in the number of hooks 1502. Moreover, there is no particular limitation in the position of the hooks 1502.

In this embodiment, the sensor unit 1500 can be attached to and detached from the scraper 1010. Thus, since the worker can remove the sensor unit 1500 from the scraper 1010, the scraper 1010 and the sensor unit 1500 can be replaced easily, and the cleanliness of the recovery operation can be maintained.

(5) Supplementary Notes

The foregoing embodiment includes, for example, the following subject matter.

While the foregoing embodiment explained a case of applying the present invention to a digitalization system, the present invention is not limited thereto, and may be broadly applied to various other systems, devices, methods, and programs. Moreover, without limitation to cell culture, the present invention can be broadly applied to manufacturing, games, and sports.

Moreover, while the foregoing embodiment explained a case of adopting a structure (T-shaped structure) in which the width of the blade is greater than the thickness (diameter) of the handle 211, the present invention is not limited thereto, and adopted may be a structure in which the thickness of the handle 211 and the width of the blade are the same, or a structure in which the width of the blade is shorter than the thickness of the handle 211.

Moreover, while the foregoing embodiment explained a case of the blade 212 being a fixed type, the present invention is not limited thereto, and the blade 212 may also be a movable type.

Moreover, while the foregoing embodiment explained a case of the scraper 110 being a rod shape, the present invention is not limited thereto, and the tip part 214 of the scraper 110 may be curved.

Moreover, in the foregoing embodiment, the gripping part 213 of the scraper 110 may be provided with unevenness for slip resistance so that the user can easily apply force and easily grip the gripping part 213 of the scraper 110.

Moreover, while the foregoing embodiment explained a case of the notification unit 405 being provided to the stand 130, the present invention is not limited thereto, and the notification unit 405 may also be provided to the tip part 214 of the scraper 110.

Moreover, while the foregoing embodiment explained a case of using the bend sensor 111 as the detection sensor for detecting the deformation of the scraper 110, the present invention is not limited thereto, and, in substitute for the bend sensor 111, a sensor for detecting the twisting of the scraper 110 may be used, or a sensor for detecting the expansion and contraction of the scraper 110 may be used.

Moreover, while the foregoing embodiment explained a case of using the pressure sensor 131 in the stand 130, the present invention is not limited thereto, and a gravity sensor may be used in substitute for the pressure sensor 131.

Moreover, while the foregoing embodiment explained a case of digitalizing the skills of the recovery operation using the bend sensor 111 and the pressure sensor 131, the present invention is not limited thereto, and an inertial sensor may be used in substitute for the bend sensor 111 and/or the pressure sensor 131.

Moreover, in the foregoing embodiment, the digitalization system 100 may also comprise a camera for capturing the recovery operation. In the foregoing case, the video captured by the camera and the pressing angle/pressing strength may be linked and stored. According to the foregoing configuration, the skills of the recovery operation can be more appropriately digitalized.

Moreover, in the foregoing embodiment, the determination unit 224 may perform its determination by using a determination model for determining whether the work is correct/incorrect. The determination model finds the characteristics of the work by giving consideration to the time series with regard to the sensor data to which a work label has been assigned (sensor data labeled by the time of recovery operation being designated based on human judgment). For example, the system administrator uses the computer 140 to find the characteristic time series pattern from the sensor data and automatically sort the results. Next, the sorted results are deemed the amount of characteristics, and a determination model is generated using a work label.

Note that the computer 140 may also comprise a function of recording the recovery operation using the bend sensor 111 and the pressure sensor 131, a function of displaying and trimming the recorded sensor data, and a function of automatically generating a determination model. In the foregoing case, the computer 140 foremost acquires and records sensor data for a given period of time before commencement and after termination of the recovery operation implemented as a result of the worker performing work of a predetermined work description and the system administrator operating the recording button on the application. Next, the system administrator designates and trims only the range of the recovery operation while viewing the characteristics of the sensor data on the application. Here, the system administrator registers whether the bodily movement is a correct bodily movement (OK) or an erroneous bodily movement (NG) of the designated recovery operation. When one or more trimmed data are created and then the learning button on the application is pressed, a determination model is automatically generated.

Moreover, in the foregoing explanation, information of programs, tables and files for realizing the respective functions may be stored in a memory, a hard disk, an SSD (Solid State Drive) or any other storage device, or in an IC card, an SD card, a DVD or any other recording medium.

The foregoing embodiment includes, for example, the following characteristic configurations.

A digitalization system (digitalization system 100) comprises a first sensor (bend sensor, strain gauge, etc.) mounted on a work tool (instrument, tool, scraper, etc.) and which detects a deformation (bending, expansion and contraction, twisting, strain) of the work tool when the work tool is pressed against a work target (for example, product, component, container such as a laboratory dish); a second sensor (pressure sensor, gravity sensor, etc.) which detects a force applied to the work target or a force applied to the work tool when the work tool is pressed against the work target; and a computer (for example, computer 140) which calculates an angle of a corner formed with the work tool and the work target (for example, corner 8 formed with the scraper 110 and the laboratory dish 120) based on sensor values acquired with the first sensor, and calculates a force (for example, force F applied by the scraper 110 in the vertical direction of the laboratory dish 120) applied to the work target when the work tool is pressed against the work target based on sensor values acquired with the second sensor.

With the foregoing configuration, the skills of delicate work can be digitalized, for example, by calculating the angle of the corner formed with the work tool and the work target and the force applied to the work target when the work tool is pressed against the work target.

The digitalization system further comprises a stand (for example, stand 130) on which the work target can be mounted, the second sensor is provided to a bottom part of the stand, and the second sensor detects, as the force applied to the work target, a force of the stand pressing a work table on which the stand is placed.

With the foregoing configuration, since the second sensor is provided to the stand and the force applied to the work table from the stand is detected, it is possible to indirectly calculate the force applied to the work target when the work tool is pressed against the work target.

The stand comprises a concave part (for example, concave part) in which the work target can be attached thereto and detached therefrom (for example, refer to FIG. 5).

With the foregoing configuration, since the work target is detachable, if the stand becomes dirty or the stand becomes damaged, the stand can be easily replaced. For example, in a work environment in which stand-derived contamination, such as the inclusion of minute foreign substances, is not tolerated, the cleanliness of the work environment can be maintained.

The stand comprises a mechanism (for example, rubber ring 401, suction port 402, and backflow prevention valve 403) for vacuum-sucking the work target.

With the foregoing configuration, since the work target is fixed to the stand based on vacuum suction, it is possible to avoid a situation where the work target comes free from the stand when the work tool is pressed against the work target.

The computer (for example, determination unit 224) compares the angle formed with the work tool and the work target and the force applied to the work target when the work tool is pressed against the work target with data indicating standard work, and thereby determines whether the work in which the work tool is pressed against the work target is correct/incorrect, and the stand includes a notification unit (for example, notification unit 405) which notifies a result of a determination by the computer.

With the foregoing configuration, since whether the work is correct/incorrect is determined and notified, for example, the worker can correct the work and efficiently perform the work. Since the foregoing notification is performed on the stand on which the work target, which is being observed by the worker, is mounted, the worker can easily notice the result of the determination.

The digitalization system further comprises an ornament (for example, glove with built-in sensors 900) that can be worn on a worker's hand, the second sensor is provided to the ornament, and the second sensor detects, as the force applied to the work tool, a force applied to the worker's hand (for example, thumb, index finger, middle finger) when the worker performs work using the work tool.

With the foregoing configuration, for example, even in a work environment not equipped with a stand comprising a second sensor, it is possible to calculate the force applied to the work target when the work tool is pressed against the work target.

The computer (for example, determination unit 224) compares the angle formed with the work tool and the work target and the force applied to the work target when the work tool is pressed against the work target with data indicating standard work, and thereby determines whether the work in which the work tool is pressed against the work target is correct/incorrect, and the ornament includes a notification unit (for example, vibrator) which notifies a result of a determination by the computer.

With the foregoing configuration, since whether the work is correct/incorrect is determined and notified, for example, the worker can correct the work and efficiently perform the work. Since the foregoing notification is performed on the ornament worn by the worker, the worker can easily notice the result of the determination.

The work tool is a rod-shaped tool, and, in work performed by a worker, one end part of the work tool is gripped by the worker, and another end part of the work tool contacts the work target (for example, refer to FIG. 7 and FIG. 8).

With the foregoing configuration, since work is performed by one end part of the work tool being gripped by the worker and the other end part of the work tool contacting the work target, deformation of the work tool can be efficiently obtained.

The work tool is a scraper (for example, scraper 110, scraper 1010), and the work target is a laboratory dish (for example, laboratory dish 120).

According to the foregoing configuration, since the angle of the corner formed with the scraper and the laboratory dish and the force applied to the laboratory dish when the scraper is pressed against the laboratory dish are calculated, for example, the skills of the recovery operation in the field of cell culture can be digitalized.

A film (for example, film 1022, glue film, self-adhesive film) having adhesive strength is provided to the first sensor so that the first sensor can be attached to and detached from the work tool (for example, refer to FIG. 10). A hook (for example, hook 1502) is provided to the first sensor so that the first sensor can be attached to and detached from the work tool (for example, refer to FIG. 15).

With the foregoing configuration, since the first sensor is detachable, if the first sensor becomes dirty or the first sensor becomes damaged, the first sensor can be easily replaced. For example, in a work environment in which first sensor-derived contamination, such as the inclusion of minute foreign substances, is not tolerated, the cleanliness of the work environment can be maintained.

The digitalization system further comprises a suspension stand (for example, suspension stand 1200) for suspending the first sensor, a magnet (for example, magnet 1024) is provided to another end of a signal line (for example, signal line 1023) to which the first sensor is connected, and a magnet (for example, magnet 1204), to which a signal line (for example, signal line 1203) for communicating with the computer is connected, is provided to a suspending part (for example, arm part) of the suspension stand.

With the foregoing configuration, since the first sensor is suspended with a magnet, the first sensor and the work tool to which the first sensor has been mounted can be stored, and these can be easily attached and detached.

A stand (for example, stand 130) comprises a bottom part (for example, bottom part 501), a peripheral wall part (for example, peripheral wall part 502) which is formed at an outer edge part of the bottom part and which as a concave part in which a work target can be attached thereto and detached therefrom, a sensor (for example, pressure sensor 131, gravity sensor) which is provided to the bottom part and which detects, as a force applied to the work target when a work tool is pressed against the work target mounted on the concave part, a force of the bottom part pressing the work table in contact with the bottom part, and a communication device (for example, communication device, printed circuit board 404) which sends sensor values obtained with the sensor to a computer (for example, computer 140) which calculates a force applied to the work target when the work tool is pressed against the work target based on the sensor values.

A bend sensor (for example, bend sensor 1021) comprises a mechanism (for example, film 1022 having adhesive strength, hook 1502) that can be attached to and detached from a work tool, and a resistor which increases a resistance value as bending of the work tool when the the work tool is pressed against a work target increases.

A magnet (for example, magnet 1024) is provided to another end of a signal line (for example, signal line 1023) to which the bend sensor is connected, and, in a suspension stand (for example, suspension stand 1200) for suspending the bend sensor, a magnet (for example, magnet 1204), to which is connected a signal line (for example, signal line 1203) for communicating with a computer (for example, computer 140) which calculates an angle of a corner formed with the work tool and the work target based on sensor values acquired with bend sensor, is provided to a suspending part (for example, arm part) of the suspension stand.

Moreover, the foregoing configurations may be suitably changed, rearranged, combined or omitted to the extent that such change, rearrangement, combination or omission does not exceed the subject matter of the present invention.

REFERENCE SIGNS LIST

100 . . . digitalization system

The invention claimed is:

1. A digitalization system, comprising:
a first sensor mounted on a work tool and which detects a deformation of the work tool when the work tool is pressed against a work target;
a second sensor which detects a force applied to the work target or a force applied to the work tool when the work tool is pressed against the work target;
a computer which calculates an angle of a corner formed with the work tool and the work target based on sensor values acquired with the first sensor, and calculates a force applied to the work target when the work tool is pressed against the work target based on sensor values acquired with the second sensor; and
a stand on which the work target can be mounted, the stand comprises at least one of a concave part in which the work target can be attached thereto and detached therefrom or a mechanism for vacuum-sucking the work target,
wherein the second sensor is provided to a bottom part of the stand, and
wherein the second sensor detects, as the force applied to the work target, a force of the stand pressing a work table on which the stand is placed.

2. The digitalization system according to claim 1, wherein:
the computer compares the angle formed with the work tool and the work target and the force applied to the work target when the work tool is pressed against the work target with data indicating standard work, and thereby determines whether the work in which the work tool is pressed against the work target is correct/incorrect; and
the stand includes a notification unit which notifies a result of a determination by the computer.

3. The digitalization system according to claim 1, further comprising:
an ornament that can be worn on a worker's hand, wherein:
the second sensor is provided to the ornament; and
the second sensor detects, as the force applied to the work tool, a force applied to the worker's hand when the worker performs work using the work tool.

4. The digitalization system according to claim 3, wherein the computer compares the angle formed with the work tool and the work target and the force applied to the work target when the work tool is pressed against the work target with data indicating standard work, and thereby determines whether
the work in which the work tool is pressed against the work target is correct/incorrect; and
the ornament includes a notification unit which notifies a result of a determination by the computer.

5. The digitalization system according to claim 1, wherein:
the work tool is a rod-shaped tool; and
in work performed by a worker, one end part of the work tool is gripped by the worker, and another end part of the work tool contacts the work target.

6. A digitalization system, comprising:
a first sensor mounted on a work tool and which detects a deformation of the work tool when the work tool is pressed against a work target
a second sensor which detects a force applied to the work target or a force applied to the work tool when the work tool is pressed against the work target; and
a computer which calculates an angle of a corner formed with the work tool and the work target based on sensor values acquired with the first sensor, and calculates a force applied to the work target when the work tool is pressed against the work target based on sensor values acquired with the second sensor, wherein:
the work tool is a scraper, and
the work target is a laboratory dish.

7. The digitalization system according to claim 1, wherein a film having adhesive strength is provided to the first sensor so that the first sensor can be attached to and detached from the work tool.

8. The digitalization system according to claim 1, wherein a hook is provided to the first sensor so that the first sensor can be attached to and detached from the work tool.

9. A digitalization system, comprising:
a first sensor mounted on a work tool and which detects a deformation of the work tool when the work tool is pressed against a work target
a second sensor which detects a force applied to the work target or a force applied to the work tool when the work tool is pressed against the work target;
a computer which calculates an angle of a corner formed with the work tool and the work target based on sensor values acquired with the first sensor, and calculates a force applied to the work target when the work tool is pressed against the work target based on sensor values acquired with the second sensor; and
a suspension stand for suspending the first sensor, wherein:
a magnet is provided to another end of a signal line to which the first sensor is connected, and
a magnet, to which a signal line for communicating with the computer is connected, is provided to a suspending part of the suspension stand.

* * * * *